United States Patent
Baek

(10) Patent No.: US 11,272,680 B2
(45) Date of Patent: Mar. 15, 2022

(54) PEPPER VARIETY NUN 89006 PPS

(71) Applicant: NUNHEMS B.V., Nunhem (NL)

(72) Inventor: UnDon Baek, Anseong-si (KR)

(73) Assignee: NUNHEMS B.V., Nunhem (NL)

( * ) Notice: Subject to any disclaimer, the term of this patent is extended or adjusted under 35 U.S.C. 154(b) by 280 days.

(21) Appl. No.: 16/504,004

(22) Filed: Jul. 5, 2019

(65) Prior Publication Data

US 2019/0357492 A1 Nov. 28, 2019

Related U.S. Application Data

(63) Continuation-in-part of application No. 16/195,315, filed on Nov. 19, 2018, now abandoned.

(60) Provisional application No. 62/667,156, filed on May 4, 2018.

(51) Int. Cl.
  *A01H 5/10* (2018.01)
  *A01H 6/82* (2018.01)
  *A01H 5/08* (2018.01)

(52) U.S. Cl.
  CPC .............. *A01H 6/822* (2018.05); *A01H 5/08* (2013.01)

(58) Field of Classification Search
  None
  See application file for complete search history.

(56) References Cited

U.S. PATENT DOCUMENTS

| | | |
|---|---|---|
| 8,492,619 B2 | 7/2013 | Bar et al. |
| 2006/0037100 A1 | 2/2006 | Kim et al. |
| 2015/0126380 A1 | 5/2015 | Van Dun |
| 2015/0245570 A1 | 9/2015 | Vogelaar et al. |

OTHER PUBLICATIONS

Poehlman et al., 1995, Methods in Plant Breeding IV, Iowa State Press, pp. 1-494, selected pp. 157, 159-180.*
Barbara Pleasant, How to Grow Peppers in Containers, GrowVeg, published Jun. 9, 2016, available at https://www.growveg.com/guides/how-to-grow-peppers-in-containers/, last accessed May 7, 2021.*
"Bell and Chile Peppers", Western Institute for Food Safety and Security, 2016, pp. 1-7.
"Guidelines for the Conduct of Tests for Distinctness, Uniformity and Stability", UPOV, International Union for the protection of new variety of plants, Geneva, UPOV Code: CAPSI_ANN (*Capsicum annuum* L.), Revised on Sep. 20, 2018, 52 pages.
"Objective Description of Variety Pepper (*Capsicum* spp.)", US Department of Agriculture, Agricultural Marketing Service Science and Technology Plant Variety Protection Office, 2015, 4 pages.
Hartz, et al., "Bell Pepper Production in California", University of California—Agriculture and Natural Resources, Publication 7217, 2008, pp. 1-4.
Ince, et al., "Genetic Relationships Within and Between *Capsicum* Species", Biochemical Genetics, vol. 48, Issue 1-2, Feb. 2010, pp. 83-95.
Kim, et al., "Callus growth and plant regeneration in diverse cultivars of cucumber (*Cucumis sativus* L.)", Plant Cell, Tissue and Organ Culture, vol. 12, Issue 1, Mar. 1988, pp. 67-74.
Kothari, et al., "Chilli peppers—A review on tissue culture and transgenesis", Biotechnology Advances, vol. 28, Issue 1, Jan.-Feb. 2010, pp. 35-48.
Martin, et al., "Identification of markers linked to agronomic traits in globe artichoke", Australian Journal of Crop Science, vol. 1, Issue 2, 2008, pp. 43-46.
Needleman, et al., "A general method applicable to the search for similarities in the amino acid sequence of two proteins", Journal of Molecular Biology, vol. 48, Issue 3, Mar. 28, 1970, pp. 443-453.
Nikolovaa, "Diploidization of cucumber (*Cucumis sativus* L.) haploids by colchicine treatment", Acta Societatis Botanicorum Poloniae, vol. 65, Issue 3-4, 1996, pp. 311-317.
Rice, et al., "EMBOSS: The European Molecular Biology Open Software Suite", Trends in Genetics, vol. 16, Issue 6, Jun. 2000, pp. 276-277.
Tiwari, et al., "Parthenocarpic potential in *Capsicum annuum*L. is enhanced by carpelloid structures and controlled by a single recessive gene", BMC Plant Biology, vol. 11, Issue 143, 2011, pp. 1-14.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, 2014, pp. 761-772.

* cited by examiner

*Primary Examiner* — Bratislav Stankovic
(74) *Attorney, Agent, or Firm* — Arent Fox LLP

(57) ABSTRACT

The disclosure provides a new and distinct pepper variety NUN 89006 PPS as well as seeds and plants and fruits thereof. NUN 89006 PPS is a yellow, mini sweet pointed sweet pepper variety for the snacking segment, comprising resistance to Pepper Mild Mottle Virus (PMMoV) Pathotype 0, and/or to Potato Y Virus Pathotype 0 and Pathotype 1.

23 Claims, 4 Drawing Sheets

PEPPER VARIETY NUN 89006 PPS

CROSS REFERENCE TO RELATED APPLICATION

The application is a continuation-in-part of U.S. patent application Ser. No. 16/195,315, filed on Nov. 19, 2018, which claims priority to U.S. Provisional Application No. 62/667,156, filed May 4, 2018, which are hereby incorporated by reference in their entireties.

FIELD OF THE DISCLOSURE

The disclosure relates to the field of plant breeding and, more specifically, to the pepper variety NUN 89006 PPS. The disclosure further relates to vegetative reproductions of pepper variety NUN 89006 PPS, methods for tissue culture of pepper variety NUN 89006 PPS, and methods for regenerating a plant from such a tissue culture and also to phenotypic variants of pepper variety NUN 89006 PPS.

BACKGROUND

The goal of plant breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species that has been subject to such breeding programs and is of particular value is the pepper. Pepper (*Capsicum* spp.) is naturally a diploid and the basic chromosome number of the genus is x=12, most are 2n=2x=24, including the cultivated ones. A few wild species have 2n=26. Ploidy changes (both tetraploidy and haploidy) are relatively easy to induce in *Capsicum* species. Doubled haploids have proved particularly valuable in the analysis of the genetically complex basis of some resistances to pests and diseases.

The genus *Capsicum* originated in American tropics. The fruit of most species of *Capsicum* produce a strong burning sensation (pungency or spiciness) in the mouth of the unaccustomed eater due to the presence of capsaicin (methyl vanillyl nonenamide), a lipophilic chemical, making it as an important spice commodity. Capsaicin can be present in large quantities in the placental tissue (which holds the seeds), the internal membranes, and to a lesser extent, the other fleshy parts of the fruits of plants in this genus. The seeds themselves do not produce any capsaicin. The amount of capsaicin in the fruit is highly variable and dependent on genetics and environment, giving almost all types of *Capsicum* varied amounts of perceived heat.

The most recognizable *Capsicum* without capsaicin is the bell pepper, a cultivar of *Capsicum annuum*, which has a zero rating on the Scoville scale. The lack of capsaicin in bell peppers is due to a recessive gene that eliminates capsaicin and, consequently, the "hot" taste usually associated with the rest of the *Capsicum* family.

Pepper can be classified according to its target market: fresh market and processing peppers. Peppers for the fresh market require that the fruits are firm, shiny and have fresh green calyx and stem. They are typically consumed fresh as a snack or used in salad or sandwiches or as a cooked vegetable. On the other hand, processing peppers are used for freezing or dehydrating and can be dried, ground as spices and processed, e.g., pickled, canned, brined or in salsas.

Majority of the peppers produced in the USA is the bell pepper (i.e., sweet pepper), which are mainly marketed fresh. California and Florida are the lead producers of bell peppers. Bell peppers are available year-round with supply at the greatest volume from May to July and March to April in California and Florida, respectively. Bulk of the bell peppers grown and harvested are green, but premium is given to colored bell peppers (i.e., red, yellow).

Both hybrids and open-pollinated varieties are used for production in the US, with a growing trend in the use of seeded hybrid varieties. Hybrid varieties offer the advantages of easy combination of dominant and recessive traits, such as disease resistance, from a set of inbred parents, as well as careful control of parentage.

Advances in biotechnology have also resulted in genetically engineered pepper plants with improved traits. For example, fungal resistant pepper plants comprising a PepEST or PepDef gene where the expression of the nucleic acid sequence in the plant resulted in increased resistance to fungal infection, see e.g., U.S. Pub. No. 2006/0037100, which hereby incorporated by reference in its entirety.

While breeding efforts to date have provided a number of useful pepper varieties with beneficial traits, there remains a great need in the art for new varieties with further improved traits. Such plants would benefit farmers and consumers alike by improving crop yields and/or quality. Breeding objectives include resistance to pests and diseases, improvement of fruit quality, protection against biotic and abiotic stresses, varying the color, texture and flavor of the fruit, optimizing flesh thickness, yield, suitability to various climatic circumstances, heat, solid content (% dry matter), or sugar content.

SUMMARY OF VARIOUS ASPECTS OF THE DISCLOSURE

The disclosure provides for a pepper variety NUN 89006 PPS, products thereof, and methods of using the same. NUN 89006 PPS is a yellow, mini sweet pointed sweet pepper variety for the snacking segment. It is suitable for early harvest with concentrated fruit set.

In one aspect, the disclosure provides a seed of pepper variety NUN 89006 PPS, wherein a representative sample of said seed has been deposited under Accession Number NCIMB 43267. The disclosure also provides for a plurality of seeds of pepper variety NUN 89006 PPS. The pepper seed of variety NUN 89006 PPS may be provided as an essentially homogeneous population of pepper seed. The population of seed of pepper variety NUN 89006 PPS may be particularly defined as being essentially free from other seed. The seed population may be grown into plants to provide an essentially homogeneous population of pepper plants as described herein.

The disclosure also provides a plant grown from a seed of pepper variety NUN 89006 PPS and a plant part thereof. In another aspect, the disclosure provides for a hybrid variety of pepper called NUN 89006 PPS. The disclosure also provides for a progeny of pepper variety NUN 89006 PPS. In another aspect, the disclosure provides a plant or a progeny retaining all or all but one, two or three of the "distinguishing characteristics" or all or all but one, two or three of the "morphological and physiological characteristics" of pepper variety NUN 89006 PPS and methods for producing that plant or progeny.

In one aspect, the disclosure provides a plant or a progeny having all the physiological and morphological characteristics of variety NUN 89006 PPS when grown under the same environmental conditions. In another aspect, the plant or progeny has all or all but one, two or three of the physiological and morphological characteristics of pepper variety NUN 89006 PPS when measured under the same environmental conditions and e.g., evaluated at significance levels of 1%, 5% or 10% significance (which can also be expressed as a p-value) for quantitative characteristics, wherein a representative sample of seed of variety NUN 89006 PPS has been deposited under Accession Number NCIMB 43267. In another aspect, the plant or progeny has all or all but one, two or three of the physiological and morphological characteristics as listed in Tables 1, 2, and 3 for variety NUN 89006 PPS when measured under the same environmental conditions and e.g., evaluated at significance levels of 1%, 5% or 10% significance (which can also be expressed as a p-value) for quantitative characteristics.

In another aspect, a plant of variety NUN 89006 PPS or a progeny thereof has 15, 16, or more or all of the following distinguishing characteristics as shown in Table 4: 1) shorter stem length from cotyledon to $1^{st}$ flower; 2) shorter $3^{rd}$ internode length; 3) larger mature leaf width; 4) larger petiole width; 5) larger flower diameter; 6) larger calyx diameter; 7) longer mature fruit length; 8) less fruit per plant; 9) heavier mature fruit weight; 10) less locules per fruit; 11) longer seed cavity length; 12) longer placenta length; 13) more seeds per fruit; 14) greyish olive green immature fruit color; 15) more vivid orange yellow mature fruit color; 16) greyish olive green leaf color; and 17) slightly less erect plant attitude.

In another aspect, the plant of variety NUN 89006 PPS or a progeny thereof comprises resistance to Pepper Mild Mottle Virus (PMMoV) Pathotype 0, and/or to Potato Y Virus Pathotype 0 and Pathotype 1, measured according to UPOV standards described in TG/76/8.

The disclosure provides for a plant part obtained from variety NUN 89006 PPS, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a scion, a stock, a rootstock, a pistil, an anther, or a flower or a part thereof. Fruits are particularly important plant parts. In a further aspect, the plant part obtained from variety NUN 89006 PPS is a cell, optionally a cell in a cell or tissue culture. That cell may be grown into a plant of variety NUN 89006 PPS.

The disclosure also provides a cell culture of pepper variety NUN 89006 PPS, and a plant regenerated from pepper variety NUN 89006 PPS, which plant has all the characteristics of pepper variety NUN 89006 PPS, when grown under the same environmental conditions, as well as methods for culturing and regenerating pepper variety NUN 89006 PPS. Alternatively, a regenerated plant may have one characteristic that is different from pepper variety NUN 89006 PPS.

The disclosure further provides a vegetatively propagated plant of variety NUN 89006 PPS having all or all but one, two or three of the morphological and physiological characteristics of pepper variety NUN 89006 PPS, when grown under the same environmental conditions.

The disclosure furthermore provides a pepper fruit produced on a plant grown from a seed of pepper variety NUN 89006 PPS.

In another aspect, the disclosure provides a seed growing or grown on a plant of variety NUN 89006 PPS (i.e., produced after pollination of the flower of pepper variety NUN 89006 PPS).

DEFINITIONS

Figure 1:
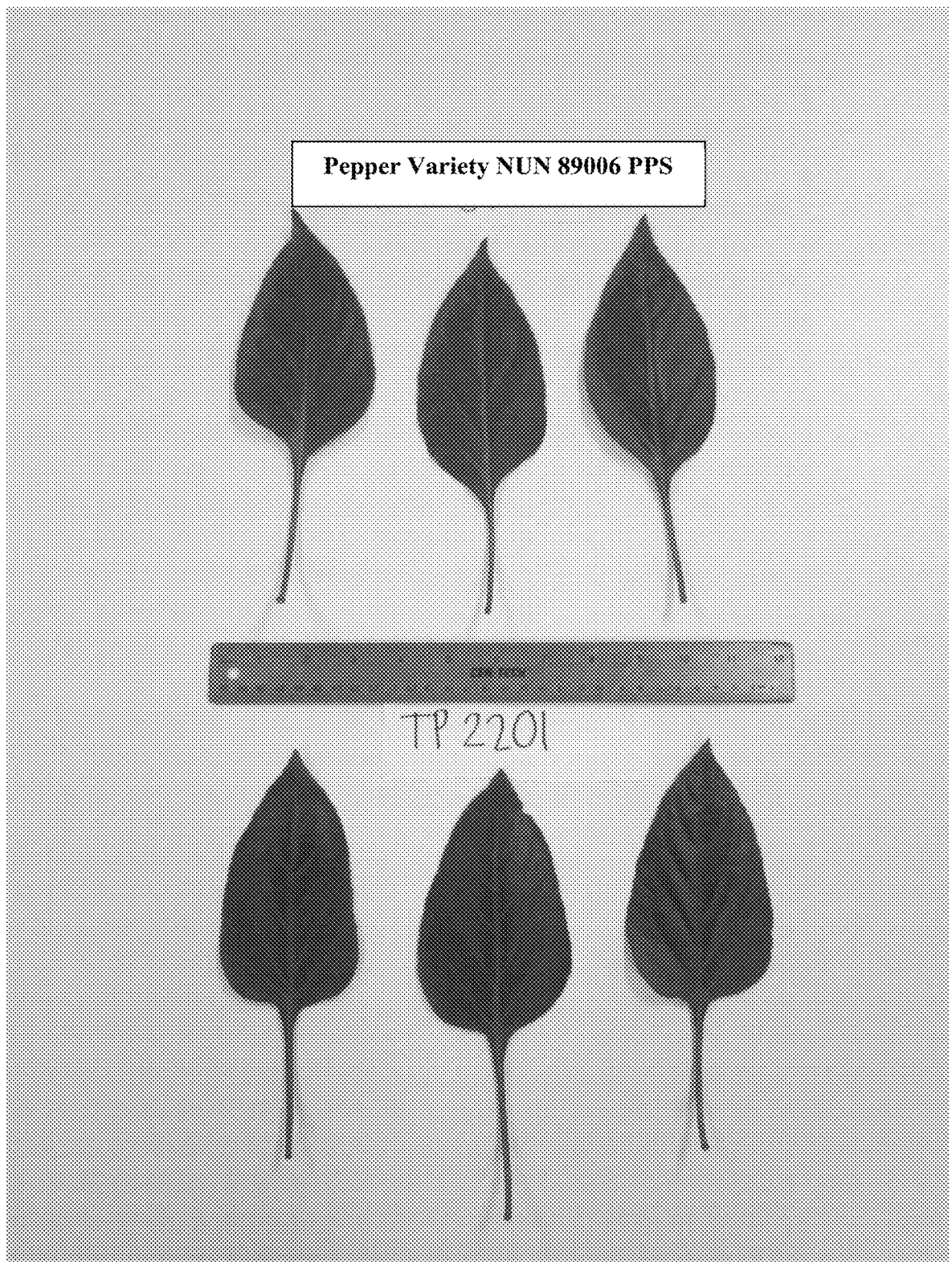
FIG. 1 shows the mature leaf (top) of pepper variety NUN 89006 PPS and the Reference Variety.
Figure 2:
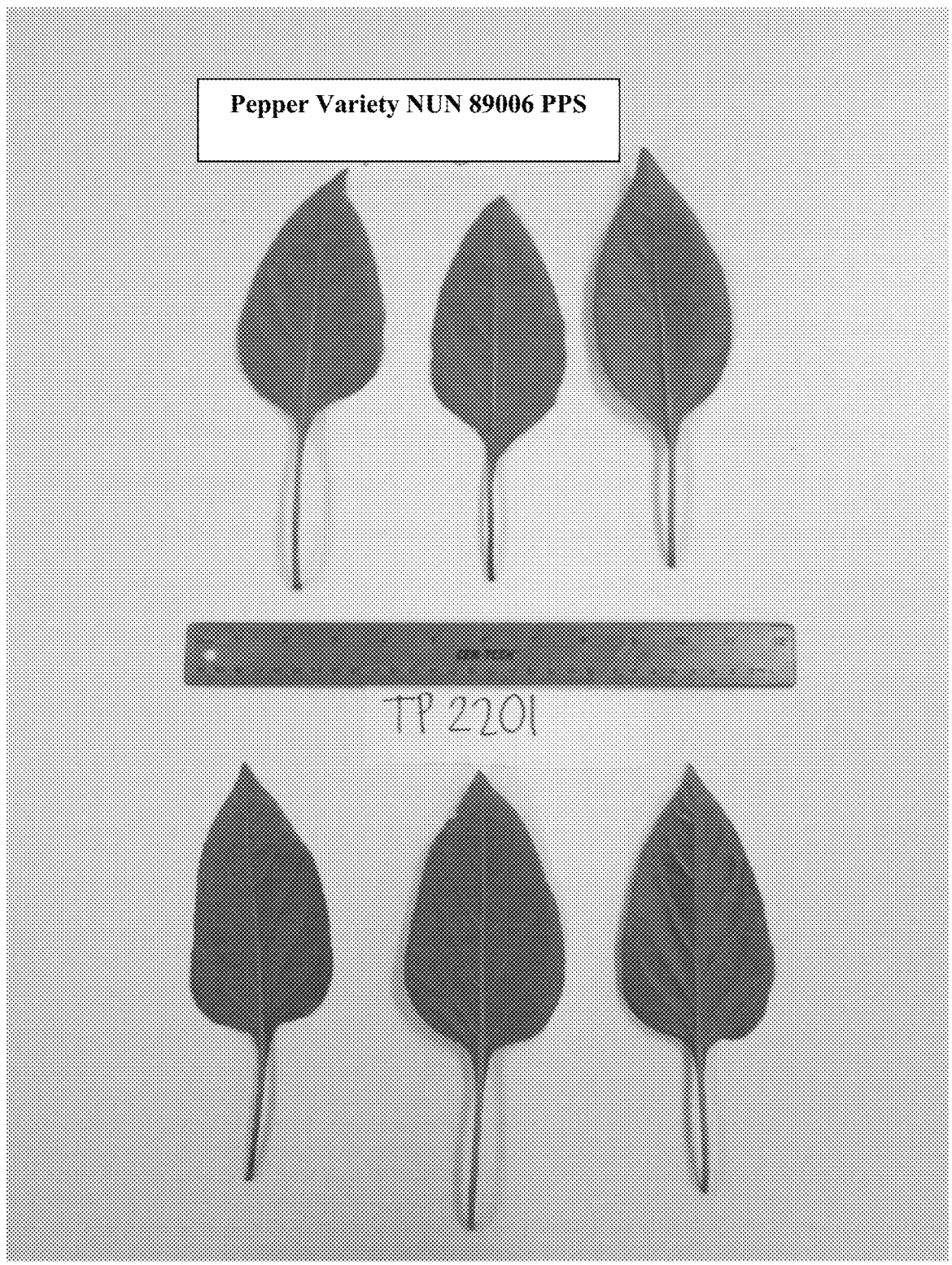
FIG. 2 shows the mature leaf (bottom) of pepper variety NUN 89006 PPS and the Reference Variety.
Figure 3:
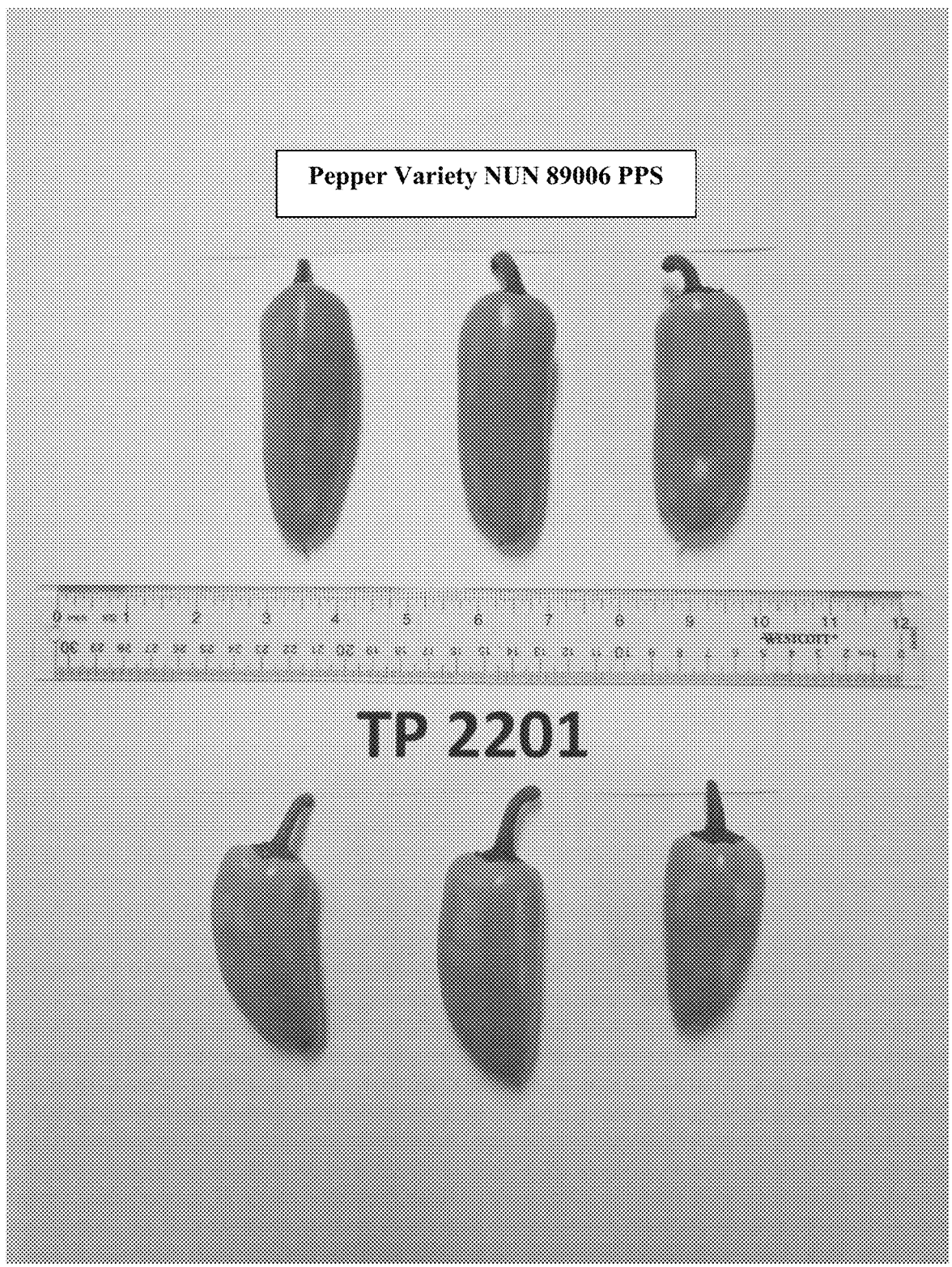
FIG. 3 shows the whole mature fruit of pepper variety NUN 89006 PPS and the Reference Variety.
Figure 4:
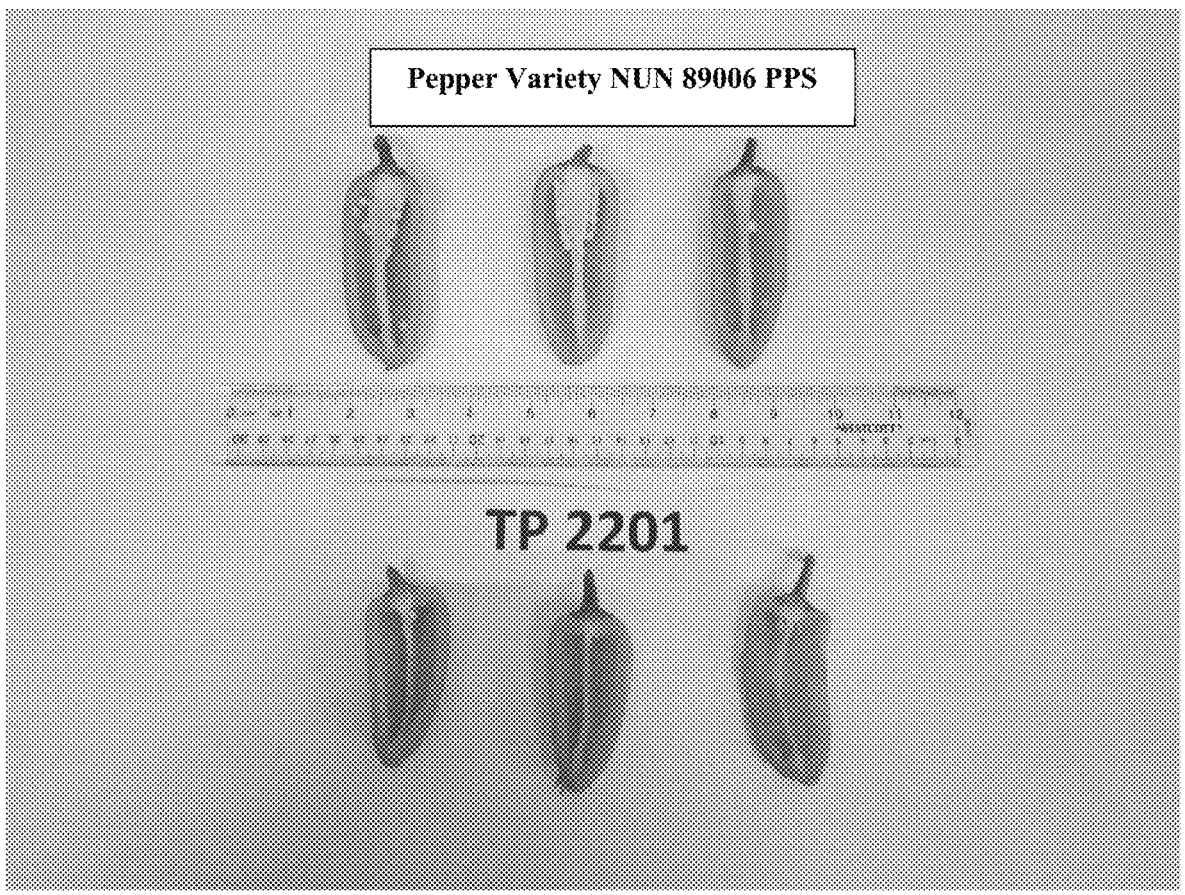
FIG. 4 shows the cross-section of mature fruit of pepper variety NUN 89006 PPS and the Reference Variety.

"Pepper" refers herein to plants of the species *Capsicum annuum* or *frutescens*, and fruits thereof. The most commonly eaten part of a pepper is the fruit or berry. The fruit comprises a stem or peduncle or pedicel, calyx, placenta, fruit wall, veins, shoulder, base, apex, locule or lobe, septa, exocarp, mesocarp, endocarp, pericarp, optionally secondary peppers, optionally capsaicin glands and optionally seed. The stem or peduncle or pedicel, calyx, placenta, fruit wall, veins, shoulder, base, apex, locule or lobe, septa, exocarp, mesocarp, endocarp, pericarp, secondary peppers, capsaicin glands and seedcoat of the seed are maternal tissues, and thus they are genetically identical to the plant on which they grow.

"Cultivated pepper" refers to plants of *Capsicum annuum*, or a closely related species, e.g., varieties, breeding lines or cultivars of the species *C. annuum* as well as crossbreds thereof, or crossbreds with other *Capsicum* species, cultivated by humans and having good agronomic characteristics.

The terms "pepper plant designated NUN 89006 PPS," "NUN 89006 PPS," "NUN 89006," "NUN 89006 F1," "89006 PPS," "pepper 89006," or "Tapuni" are used interchangeably herein and refer to a pepper plant of variety NUN 89006 PPS, representative seed of which has been deposited under Accession Number NCIMB 43267.

A "seed of NUN 89006 PPS" refers to a pepper seed which can be grown into a plant of variety NUN 89006 PPS, wherein a representative sample of viable seed of NUN 89006 PPS has been deposited under Accession Number NCIMB 43267. A seed can be in any stage of maturity, for example, a mature, viable seed, or an immature, non-viable seed. A seed comprises an embryo and maternal tissues.

An "embryo of NUN 89006 PPS" refers to an "F1 hybrid embryo" as present in a seed of pepper variety NUN 89006 PPS, a representative sample of said seed of said pepper variety has been deposited under Accession Number NCIMB 43267.

A "seed grown on NUN 89006 PPS" refers to a seed grown on a mature plant of variety NUN 89006 PPS or inside a fruit of pepper variety NUN 89006 PPS. The "seed grown on NUN 89006 PPS" contains tissues and DNA of the maternal parent, pepper variety NUN 89006 PPS. The "seed grown on NUN 89006 PPS" contains an F2 embryo. When said seed is planted, it grows into a first generation progeny plant of variety NUN 89006 PPS.

A "fruit of NUN 89006 PPS" refers to a fruit containing maternal tissues of pepper variety NUN 89006 PPS as deposited under Accession Number NCIMB 43267. In one aspect, the fruit does not contain seed, i.e., the fruit is parthenocarpic. The skilled person is familiar with methods for inducing parthenocarpy. Those methods comprise chemically or genetically inducing parthenocarpy. Compounds suitable for chemically inducing parthenocarpy include auxins, gibberellins and cytokinins. Genetic parthenocarpy can be induced by CaARF8 mutants (see, e.g., Tiwari et al., *BMC Plant Biology* 2011, 11:143 DOI: 10.1186/1471-2229-11-143 or U.S. Pat. No. 8,492,619, which are herein incorporated by reference in their entireties). A fruit can be in any stage of maturity, for example, comprising viable seed or comprising immature non-viable seed.

An "essentially homogeneous population of pepper seed" is a population of seeds where at least 97%, 98%, 99% or more of the total population of seed are seed of pepper variety NUN 89006 PPS.

An "essentially homogeneous population of pepper plants" is a population of plants where at least 97%, 98%, 99% or more of the total population of plants are plants of pepper variety NUN 89006 PPS.

The phrase "essentially free from other seed" refers to a population of seed where less than 3%, 2%, 1% or less of the total population of seed is seed that is not a pepper seed or, in another option, less than 3%, 2%, 1% or less of the total population of seed is seed that is not seed of pepper variety NUN 89006 PPS.

"Tissue culture" or "cell culture" refers to a composition comprising isolated cells of the same or a different type or a collection of such cells organized into parts of a plant. Tissue culture of various tissues of pepper and regeneration of plants therefrom is well known and widely published (see, e.g., Sang-Gu et al. (1988), Plant Cell, Tissue and Organ Culture 12: 67-74; Kothari et al., (2010) Biotechnology Advances 28: 35-48). Similarly, the methods of preparing a "tissue culture" or "cell culture" are well-known in the art.

"USDA descriptors" are the plant variety descriptors for pepper (*Capsicum* spp.) as published by the US Department of Agriculture, Agricultural Marketing Service, Plant Variety Protection Office, Beltsville, Md. 20705, and which can be downloaded from the world wide web at ams.usda.gov under services/plant-variety-protection/pvpo-c-forms under pepper. "Non-USDA descriptors" are other descriptors suitable for describing pepper.

"UPOV descriptors" are the plant variety descriptors described for pepper in the "Guidelines for the Conduct of Tests for Distinctness, Uniformity and Stability, TG/76/8 (Geneva 2006, revised 2015 Mar. 25 and 2018 Sep. 20), as published by UPOV (International Union for the Protection of New Varieties and Plants, and which can be downloaded from the world wide web at upov.int under edocs/tgdocs/en/tg076.pdf and is herein incorporated by reference in its entirety. Likewise, "UPOV methods" to determine specific parameters for the characterization of pepper are described at upov.int.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart 2007.

"Reference Variety for NUN 89006 PPS" refers herein to variety TP 2201, a commercial variety from Femix Seeds, which has been planted in a trial together with pepper variety NUN 89006 PPS. The characteristics of pepper variety NUN 89006 PPS were compared to the characteristics of the Reference Variety as shown in Tables 1 and 2. The UPOV characteristics of pepper variety NUN 89006 PPS are shown in Table 3. The distinguishing characteristics between pepper variety NUN 89006 PPS and the Reference Variety are shown in Table 4.

"Harvest maturity" is referred to as the stage at which a pepper fruit is ripe or ready for harvest or the optimal time to harvest the fruit for the market, for processing or for consumption. In one aspect, harvest maturity is the stage which allows proper completion of the normal ripening.

"Flavor" refers to the sensory impression of a food or other substance, especially a pepper fruit or fruit part (fruit flesh) and is determined mainly by the chemical senses of taste and smell. Flavor is influenced by texture properties and by volatile and/or non-volatile chemical components (organic acids, lipids, carbohydrates, salts, etc.).

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises one or two sets of chromosomes derived from the parent plant, e.g., from pepper variety NUN 89006 PPS. An F2 progeny produced from self-pollination of pepper variety NUN 89006 PPS, will thus comprise two sets of chromosomes derived from that variety, while an F2 progeny derived from cross-fertilization of pepper variety NUN 89006 PPS, will comprise only one set of chromosomes from said variety and the other set of chromosomes from the other parent.

"Harvested plant material" refers herein to plant parts (e.g., fruits detached from the whole plant), which have been collected for further storage and/or further use.

"Yield" means the total weight of all pepper fruits harvested per hectare of a particular line or variety. It is understood that "yield" expressed as weight of all pepper fruits harvested per hectare can be obtained by multiplying the number of plants per hectare times the "yield per plant".

"Marketable yield" means the total weight of all marketable pepper fruits, especially fruit that is not cracked, damaged or diseased, harvested per hectare of a particular line or variety. A "marketable fruit" is a fruit that has commercial value.

"Rootstock" or "stock" refers to the plant selected for its roots, in particular for the resistance of the roots to diseases or stress (e.g., heat, cold, salinity etc.). Generally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired pepper fruit.

"Stock/scion" or grafted plant refers to a pepper plant comprising a rootstock from one plant grafted to a scion from another plant.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1, 2, and 3 or "all or all but one, two or three of the physiological and morphological characteristics" of Tables 1, 2, and 3.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of variety NUN 89006 PPS, may have one or more (or all) of the physiological and/or morphological characteristics of said variety listed in Tables 1, 2, and 3, as determined at the 5% significance level (i.e., $p<0.05$) when grown under the same environmental conditions.

"Distinguishing characteristics" or "distinguishing morphological and/or physiological characteristics" refers herein to the characteristics which distinguish (i.e., are different) between the new variety and other pepper varieties, such as the Reference Variety, when grown under the same environmental conditions. The distinguishing characteristics between pepper variety NUN 89006 PPS and the Reference Variety are described herein and also can be seen in Table 4. When comparing pepper variety NUN 89006 PPS with different varieties, the distinguishing characteristics will be different. In one aspect, the distinguishing characteristics may therefore include at least one, two, three or more (or all) of the characteristics listed in Tables 1, 2, and 3. All numerical distinguishing characteristics are statistically significantly different at $p<0.05$ between pepper variety NUN 89006 PPS and the other variety, e.g., the Reference Variety.

Pepper variety NUN 89006 PPS has the following distinguishing characteristics when compared to the Reference Variety as shown in Table 4: 1) shorter stem length from cotyledon to $1^{st}$ flower; 2) shorter $3^{rd}$ internode length; 3) larger mature leaf width; 4) larger petiole width; 5) larger flower diameter; 6) larger calyx diameter; 7) longer mature fruit length; 8) less fruit per plant; 9) heavier mature fruit weight; 10) less locules per fruit; 11) longer seed cavity length; 12) longer placenta length; 13) more seeds per fruit; 14) greyish olive green immature fruit color; 15) more vivid orange yellow mature fruit color; 16) greyish olive green leaf color; and 17) slightly less erect plant attitude, where the characteristics of pepper variety NUN 89006 PPS are compared to the characteristics of Reference Variety, when grown under the same environmental conditions.

Thus, a pepper plant "comprising the distinguishing characteristics of pepper variety NUN 89006 PPS" (such as a progeny plant) refers herein to a plant which does not differ significantly from said variety in the distinguishing characteristics above. Therefore, in one aspect, a plant (such as a progeny plant of variety NUN 89006 PPS) is provided which does not differ significantly from pepper variety NUN 89006 PPS in the distinguishing characteristics above.

Similarity and differences between two different plant lines or varieties can be determined by comparing the number of morphological and/or physiological characteristics (e.g., the characteristics as listed in Tables 1, 2, and 3) that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic is considered "the same" when the values have the same "degree" or "type" when scored using USDA and/or UPOV descriptors, if the plants are grown under the same environmental conditions.

As used herein, the term "variety," "cultivated pepper," or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding, etc. as known to the breeder (i.e., methods other than genetic modification/transformation/transgenic methods), by which, for example, a genetically heritable trait can be transferred from one pepper line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 89006 PPS. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another pepper plant of the same variety or another variety or (breeding) line, or with wild pepper plants. A progeny may comprise a mutation or a transgene. A "first generation progeny" or is the progeny directly derived from, obtained from, obtainable from or derivable from the parent plant by, e.g., traditional breeding methods (selfing and/or cross-pollinating) or regeneration (optionally combined with transformation and mutation). Thus, a plant of variety NUN 89006 PPS, is the male parent, the female parent or both of a first generation progeny of that variety. Progeny may have all the physiological and morphological characteristics of pepper variety NUN 89006 PPS, when grown under the same environmental conditions and/or progeny may have (be selected for having) one or more of the distinguishing characteristics of pepper of the disclosure. Using common breeding methods such as backcrossing or recurrent selection, mutation or transformation, one or more specific characteristics may be introduced into said variety, to provide or a plant comprising all but 1, 2, or 3 or more of the morphological and physiological characteristics of pepper variety NUN 89006 PPS (as listed in Tables 1, 2, and 3).

The terms "gene converted" or "conversion plant" or "single locus converted plant" in this context refer to pepper plants which are developed by traditional breeding techniques e.g., backcrossing or via genetic engineering or through mutation breeding, wherein essentially all of the desired morphological and physiological characteristics of the parent variety or line are recovered, in addition to the one or more genes transferred into the parent via e.g., backcrossing technique (optionally including reverse breeding or reverse synthesis of breeding lines). It is understood that only the addition of a further characteristic (e.g., addition of gene conferring a further characteristic, such as a disease resistance gene), but also the replacement/modification of an existing characteristic by a different characteristic is encompassed herein.

Likewise, a "Single Locus Converted (Conversion) Plant" refers to a plant developed by plant breeding techniques comprising or consisting of mutation and/or by genetic transformation and/or by traditional breeding techniques, such as backcrossing, wherein essentially all of the desired morphological and physiological characteristics of a pepper variety are recovered in addition to the characteristics of the single locus having been transferred into the variety via the backcrossing technique. In case of a hybrid, the gene may be introduced in the male or female parental line.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for pepper variety NUN 89006 PPS. The mean, if not indicated otherwise within this application, refers to the arithmetic mean of measurements on at least 10 different, randomly selected plants of a variety or line.

DETAILED DESCRIPTION OF VARIOUS ASPECTS OF THE DISCLOSURE

The disclosure relates to a plant of variety NUN 89006 PPS, wherein a representative sample of seeds of said variety has been deposited under the Budapest Treaty, with Accession number NCIMB 43267. NUN 89006 PPS is a yellow, mini sweet pointed sweet pepper variety for the snacking segment. It is suitable for early harvest with concentrated fruit set.

The disclosure also relates to a seed of pepper variety NUN 89006 PPS, wherein a representative sample of said seed has been deposited under the Budapest Treaty, with Accession number NCIMB 43267.

In another aspect, the disclosure provides for a pepper plant part of variety NUN 89006 PPS, preferably a fruit, a representative sample of seed from said variety has been deposited under the Budapest Treaty, with Accession number NCIMB 43267.

In another aspect, a seed of hybrid variety NUN 89006 PPS is obtainable by crossing the male parent of said variety with the female parent of said variety and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of variety NUN 89006 PPS.

Also provided is a plant of pepper variety NUN 89006 PPS, or a fruit or other plant part thereof, produced from a seed, wherein a representative sample of said seeds has been deposited under the Budapest Treaty, with Accession Number NCIMB 43267.

Also a plant part obtained from variety NUN 89006 PPS, is provided, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. Fruits may be parthenocarpic, or seedless, or contain immature and/or nonviable seeds. In a further aspect, the plant part obtained from variety NUN 89006 PPS is a cell, optionally a cell in a cell or tissue culture. That cell may be grown into a plant of variety NUN 89006 PPS. A part of a variety of NUN 89006 PPS (or of progeny of said variety or of a plant having all physiological and/or morphological characteristics but one, two or three which are different from those of pepper variety NUN 89006 PPS) further encompasses any cells, tissues, organs obtainable from the seedlings or plants in any stage of maturity.

The disclosure also provides for a food or feed product or a processed product comprising or consisting of a plant part described herein. Preferably, the plant part is a pepper fruit or part thereof and/or an extract from a fruit or another plant part described herein comprising at least one cell of pepper variety NUN 89006 PPS. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of variety NUN 89006 PPS can be stored and/or processed further. The disclosure thus also provides for a food or feed product comprising one or more of such parts, such as canned, chopped, cooked, roasted, in a sauce, in a sandwich, pasted, puréed or concentrated, juiced, frozen, dried, pickled, or powdered pepper fruit from said variety or from progeny of said variety, or from a plant having all but one, two or three physiological and/or morphological characteristics of pepper variety NUN 89006 PPS.

In another aspect, the disclosure provides for a pepper fruit of variety NUN 89006 PPS, or a part of a fruit of said variety. The fruit can be in any stage of maturity, for example, immature or mature. In another aspect, the disclosure provides for a container comprising or consisting of a plurality of harvested pepper fruits or parts of fruits of said variety, or fruits of progeny thereof, or fruits of a derived variety.

In another aspect, the plant, plant part or seed of NUN 89006 PPS is inside a container, for example, containers such as cans, boxes, crates, bags, cartons, Modified Atmosphere Packaging, films (e.g., biodegradable films), etc. comprising a plant or a part of a plant (fresh and/or processed) or a seed of pepper variety NUN 89006 PPS. In a particular aspect, the container comprises a plurality of seeds, or a plurality of plant parts of variety NUN 89006 PPS.

The disclosure further relates to a pepper variety NUN 89006 PPS, which when compared to its Reference Variety has the following distinguishing characteristics as shown in Table 4: 1) shorter stem length from cotyledon to $1^{st}$ flower; 2) shorter $3^{rd}$ internode length; 3) larger mature leaf width; 4) larger petiole width; 5) larger flower diameter; 6) larger calyx diameter; 7) longer mature fruit length; 8) less fruit per plant; 9) heavier mature fruit weight; 10) less locules per fruit; 11) longer seed cavity length; 12) longer placenta length; 13) more seeds per fruit; 14) greyish olive green immature fruit color; 15) more vivid orange yellow mature fruit color; 16) greyish olive green leaf color; and 17) slightly less erect plant attitude, where the characteristics are determined at the 5% significance level for plants grown under the same environmental conditions. Also encompassed are parts of that plant.

In one aspect, a plant of variety NUN 89006 PPS or a progeny plant thereof, comprises all of the following morphological and/or physiological characteristics (i.e., average values of distinguishing characteristics, as indicated on the USDA Objective description of variety—pepper (unless indicated otherwise)) as shown in Tables 1, 2, and 3, where the characteristics are determined at the 5% significance level for plants grown under the same environmental conditions. A part of this plant is also provided.

In another aspect, pepper variety NUN 89006 PPS or a progeny thereof comprises resistance to Pepper Mild Mottle Virus (PMMoV) Pathotype 0, and/or to Potato Y Virus Pathotype 0 and Pathotype 1, measured according to UPOV standards described in TG/76/8.

The disclosure further provides a pepper plant which does not differ from the physiological and morphological characteristics of the plant of variety NUN 89006 PPS as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant.

The disclosure also provides a tissue or cell culture comprising cells of pepper variety NUN 89006 PPS. Such a tissue culture can, for example, be grown on plates or in liquid culture, or be frozen for long term storage. The cells of pepper variety NUN 89006 PPS used to start the culture can be selected from any plant part suitable for vegetative reproduction, or in a particular aspect can be one or more of an embryo, meristem, a cotyledon, a hypocotyl, pollen, a leaf, an anther, a root, a root tip, a pistil, a petiole, a flower, a fruit, seed, and/or a stem. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a pepper plant regenerated from the tissue or cell culture of pepper variety NUN 89006 PPS, wherein the regenerated plant is not significantly different from pepper variety NUN 89006 PPS in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a pepper plant regenerated from the tissue or cell culture of pepper variety NUN 89006 PPS, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same and determining whether numerical characteristics are different at the 5% significance level.

Pepper variety NUN 89006 PPS, or its progeny, or a plant having all physiological and/or morphological characteristics but one, two or three which are different from those of pepper variety NUN 89006 PPS, can also be reproduced using vegetative reproduction methods. Therefore, the disclosure provides for a method of producing a plant, or a part thereof, of variety NUN 89006 PPS, comprising vegetative propagation of said variety. Vegetative propagation comprises regenerating a whole plant from a plant part of variety NUN 89006 PPS (or from a progeny of said variety or from or a plant having all physiological and/or morphological characteristics of said variety but one, two or three different characteristics), such as a cutting, a cell culture, or a tissue culture.

The disclosure also concerns methods of vegetatively propagating a part of the plant of variety NUN 89006 PPS. In certain aspects, the method comprises the steps of: (a) collecting tissue or cells capable of being propagated from a plant described herein; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one aspect, the method further comprises step (d) growing plants from said rooted plantlets. Therefore, the method also comprises regenerating a whole plant from said part of NUN 89006 PPS. In a particular aspect, the part of the plant to be propagated is a cutting, a cell culture or a tissue culture.

The disclosure also provides for a vegetatively propagated plant of variety NUN 89006 PPS (or from progeny of said variety or from or a plant having all but one, two or three physiological and/or morphological characteristics of said variety), wherein the plant has all of the morphological and physiological characteristics of pepper variety NUN 89006 PPS, when the characteristics are determined at the 5% significance level for plants grown under the same conditions. In another aspect, the propagated plant has all but one, two or three of the morphological and physiological characteristics of pepper variety NUN 89006 PPS, when the characteristics are determined at the 5% significance level for plants grown under the same conditions. A part of said propagated plant or said propagated plant with one, two or three differences is also included.

In another aspect, the disclosure provides a method for producing a pepper plant part, preferably a fruit, comprising growing a plant of variety NUN 89006 PPS until it sets at least one fruit, and collecting the fruit. Preferably, the fruit is collected at harvest maturity. In another aspect, the fruit is collected when the seed is ripe. A plant of variety NUN 89006 PPS can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop. Stakes and plastic mulches may also be used for peppers for the fresh market, particularly, when peppers are to be harvested at mature fruit color and to promote earliness and yield. On the other hand, no stake or mulch is used for processing peppers. Moreover, pepper can also be grown entirely in greenhouses or tunnels.

In still another aspect, the disclosure provides a method of producing a pepper plant, comprising crossing a plant of pepper variety NUN 89006 PPS with a second pepper plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect of the disclosure, the first "crossing" further comprises planting seeds of a first and a second parent pepper plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect, the disclosure provides a method of producing a plant, comprising selfing a plant of variety NUN 89006 PPS one or more times, and selecting a progeny plant from said selfing. In one aspect, the progeny plant retains all the distinguishing characteristics of pepper variety NUN 89006 PPS when grown under the same environmental conditions. In a different aspect the progeny plant comprises all (or all but one, two or three) of the physiological and morphological characteristic of pepper variety NUN 89006 PPS of Tables 1, 2, and 3.

In other aspects, the disclosure provides a progeny plant of variety NUN 89006 PPS, such as a progeny plant obtained by further breeding that variety. Further breeding with the variety includes selfing that variety one or more times and/or cross-pollinating that variety with another pepper plant or variety one or more times. In particular, the disclosure provides for a progeny plant that retains all the morphological and physiological characteristics of pepper variety NUN 89006 PPS or, in another aspect, a progeny plant that retains all, or all but one, two or three, of the morphological and physiological characteristics of pepper variety NUN 89006 PPS, optionally all or all but one, two or three of the characteristics as listed in Tables 1, 2, and 3, when grown under the same environmental conditions, determined at the 5% significance level for numerical characteristics. In a particular aspect, the progeny is a first generation progeny, i.e., the ovule or the pollen (or both) used in the crossing is an ovule or pollen of variety NUN 89006 PPS, where the pollen comes from an anther of and the ovule comes from an ovary of pepper variety NUN 89006 PPS. In another aspect, the disclosure provides for a vegetative reproduction of the variety and a plant having all, or all but 1, 2, or 3 of the physiological and morphological characteristics of pepper variety NUN 89006 PPS (e.g., as listed in Tables 1, 2, and 3).

The disclosure also provides a method for collecting pollen comprising collecting pollen from a plant of variety NUN 89006 PPS. Alternatively, the method comprises growing a plant of variety NUN 89006 PPS until at least one flower contains pollen and collecting the pollen. In particular aspect, the pollen is collected when it is mature or ripe. A suitable method for collecting pollen comprises collecting anthers or the part of the anther that contains pollen, for example by cutting the anther or the part of the anther off. Pollen can be collected in a container. Optionally, collected pollen can be used to pollinate a pepper flower.

The morphological and/or physiological differences between two different individual plants of the disclosure (e.g., between pepper variety NUN 89006 PPS, and a progeny thereof) or between a plant of variety NUN 89006 PPS or progeny of said variety, or a plant having all, or all but 1, 2, or 3, of the physiological and morphological characteristics of pepper variety NUN 89006 PPS (or all, or all but 1, 2, or 3 of the characteristics as listed in Tables 1, 2, and 3) and another known variety can easily be established by growing said variety next to each other or next to the other variety (in the same field, under the same environmental conditions), preferably in several locations which are suitable for said pepper cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of pepper. Thus, the disclosure comprises pepper plant having one, two or three physiological and/or morphological characteristics which are different from those of the plant of variety NUN 89006 PPS and which otherwise has all the physiological and morphological characteristics of said variety, when determined at the 5% significance level for plants grown under the same environmental conditions. In a particular aspect, the different characteristic(s) is/are result of breeding with pepper variety NUN 89006 PPS and selection of progeny plant comprising 1, 2, or 3 characteristics which are different than in pepper variety NUN 89006 PPS. In another aspect, the different characteristic is the result of a mutation (e.g., spontaneous mutation or a human induced mutation through e.g., targeted mutagenesis or traditional mutagenesis such as chemically or radiation induced mutagenesis), or it is the result of transformation.

The morphological and physiological characteristics (and the distinguishing characteristics) of pepper variety NUN 89006 PPS are provided in Tables 1, 2, and 3. Encompassed herein is also a plant obtainable from pepper variety NUN 89006 PPS (e.g., by selfing and/or crossing and/or backcrossing with said variety and/or progeny of said variety) comprising all or all but one, two or three of the physiological and morphological characteristics of pepper variety NUN 89006 PPS listed in Tables 1, 2, and 3 as determined at the 5% significance level for numerical characteristics or identical for non-numerical characteristics when grown under the same environmental conditions and/or comprising one or more (or all; or all except one, two or three) characteristics when grown under the same environmental conditions. The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society Chart.

In yet a further aspect, the disclosure provides for a method of producing a pepper plant. The method comprises crossing a plant of variety NUN 89006 PPS, or a plant comprising all but 1, 2, or 3 of the morphological and physiological characteristics of said variety (as listed in Tables 1, 2, and 3), or a progeny plant thereof, either as male or as female parent, with a second pepper plant (or a wild relative of pepper) one or more times, and/or selfing a pepper plant of variety NUN 89006 PPS or a progeny plant thereof, one or more times, and selecting progeny from said crossing and/or selfing. The second pepper plant may, for example, be a line or variety of the species *Capsicum annuum, C. frutecens, C. baccatum, C. chinense*, or other *Capsicum* species.

The disclosure provides for methods of producing plants which retain all the morphological and physiological characteristics of a plant of variety NUN 89006 PPS. The disclosure provides also for methods of producing a plant comprising all but 1, 2, or 3 or more of the morphological and physiological characteristics of pepper variety NUN 89006 PPS (e.g., as listed in Tables 1, 2, and 3), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to pepper variety NUN 89006 PPS if its DNA fingerprint is at least 80%, 90%, 95% or 98% identical to the fingerprint of said variety. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Ince, et. al., 2010, Biochem Genet 48:83-95). The disclosure also provides a plant and a variety obtained or selected by applying these methods on pepper variety NUN 89006 PPS. Such a plant may be produced by crossing and/or selfing, or alternatively, a plant may simply be identified and selected amongst plants of said variety, or progeny of said variety, e.g., by identifying a variant within pepper variety NUN 89006 PPS, or within progeny of said variety (e.g., produced by selfing) which variant differs from said variety in one, two or three of the morphological and/or physiological characteristics (e.g., in one, two or three distinguishing characteristics), e.g., those listed in Tables 1, 2, and 3. In one aspect, the disclosure provides a pepper plant having a Jaccard's Similarity index with pepper variety NUN 89006 PPS of at least 0.8, e.g., at least 0.85, 0.9, 0.95, 0.98 or even at least 0.99.

In some aspects, the disclosure provides a pepper plant comprising genomic DNA having at least 95%, 96%, 97%, 98% or 99% sequence identity compared to the genomic DNA sequence of a plant of variety NUN 89006 PPS as deposited under Accession Number NCIMB 43267. In some aspects, the pepper plant further comprises all or all but 1, 2, or 3 of the morphological and physiological characteristics of pepper variety NUN 89006 PPS (e.g., as listed in Tables 1, 2, and 3). In other aspects, the pepper plant is a hybrid derived from a seed or plant of variety NUN 89006 PPS. In other aspects, the pepper plant further comprises all of the distinguishing characteristics of a plant of variety NUN 89006 PPS.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

The disclosure also provides methods for determining the identity of parental lines of plants described herein, in particular the identity of the female line. US2015/0126380, which is hereby incorporated by reference in its entirety, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of variety NUN 89006 PPS, is a progeny of said variety, because the seed coat of the seed is a maternal tissue genetically identical to said variety. In one aspect, the disclosure relates to a seed coat comprising maternal tissue of pepper variety NUN 89006 PPS. In another aspect, the disclosure relates to a pepper seed comprising a maternal tissue of pepper variety NUN 89006 PPS. In another particular aspect, the disclosure provides for a method of identifying the female parental line of pepper variety NUN 89006 PPS by analyzing the seed coat of a seed of that variety. In another aspect, the skilled person can determine whether a seed is grown on pepper variety NUN 89006 PPS by analyzing the seed coat of said seed.

By crossing and/or selfing, (one or more) single traits may be introduced into pepper variety NUN 89006 PPS (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into N pepper variety UN 89006 PPS by breeding with said variety.

Alternatively, a single trait converted plant or single locus converted plant of variety NUN 89006 PPS may be produced by (i) genetically transforming or mutating cells of pepper variety NUN 89006 PPS; (ii) growing the cells into a plant; and (iii) optionally selecting a plant that contains the desired single locus conversion. The skilled person is familiar with various techniques for genetically transforming a single locus in a plant cell, or mutating said cells.

Any pest or disease resistance genes may be introduced into a plant of variety NUN 89006 PPS, progeny of said variety or into a plant comprising all but 1, 2, or 3 or more of the morphological and physiological characteristics of pepper variety NUN 89006 PPS (e.g., as listed in Tables 1, 2, and 3). Resistance to one or more of the following diseases or pests may be introduced into plants of the disclosure: Cucumber Mosaic Virus, Curly Top Virus, Pepper Mild Mottle Virus, Potato Y Virus, Tobacco Etch Virus, Tobacco Mosaic Virus, Tomato Spotted Wilt Virus, Anthracnose (*Gloeosporium piperatum*), Bacterial Spot (*Xanthomonas vesicatoria*), Cercospora Leaf Spot (*Cercospora capsici*), Nematode (*Meloidogyne incognita acrita*), Phytophthora Root Rot (*Phytophthora capsici*), Ripe Rot (*Vermicularia capsici*), Southern Blight (*Sclerotium rolfsii*) and/or Verticillium Wilt (*Verticillium dahliae*). Other resistance genes, against pathogenic viruses, fungi, bacteria, nematodes, insects or other pests may also be introduced. In another aspect, the resistance is TSWV resistance.

The disclosure also provides a method for developing a pepper plant in a pepper breeding program, using a pepper plant described herein, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing pepper variety NUN 89006 PPS or progeny of said variety, or a plant comprising all but 1, 2, or 3 or more of the morphological and physiological characteristics of pepper variety NUN 89006 PPS (e.g., as listed in Tables 1, 2, and 3), with a different pepper plant, and wherein one or more offspring of the crossing are subject to one or more plant breeding techniques: recurrent selection, backcrossing, pedigree breeding, mass selection, mutation breeding and genetic marker enhanced selection (see, e.g., Martin et al. 2008, Australian Journal of Crop Science 1(2): 43-46). For breeding methods in general, see, e.g., Principles of Plant Genetics and Breeding, 2007, George Acquaah, Blackwell Publishing, ISBN-13: 978-1-4051-3646-4.

The disclosure also provides a pepper plant comprising at least a first set of the chromosomes of pepper variety NUN 89006 PPS, a sample of seed of said variety is deposited under Accession Number NCIMB 43267; optionally further comprising a single locus conversion or a mutation, wherein said plant has all of the morphological and physiological characteristics of the plant comprising at least a first set of the chromosomes of said variety. In another aspect, this single locus conversion confers a trait: yield, compact pepper, fruit quality, storage properties, color, male sterility, herbicide tolerance, insect resistance, pest resistance, disease resistance, environmental stress tolerance, modified carbohydrate metabolism, modified protein metabolism or ripening.

In one aspect, a plant of variety NUN 89006 PPS may also be mutated (by e.g., irradiation, chemical mutagenesis, heat treatment, etc.) and mutated seeds or plants may be selected in order to change one or more characteristics of said variety. Methods such as TILLING may be applied to pepper populations in order to identify mutants. Similarly, pepper variety NUN 89006 PPS may be transformed and regenerated, whereby one or more chimeric genes are introduced into the variety or into a plant comprising all but 1, 2, 3, or more of the morphological and physiological characteristics (e.g., as listed in Tables 1, 2, and 3). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into pepper variety NUN 89006 PPS, or progeny of said variety, by transforming said variety or progeny of said variety with a transgene that confers the desired trait, wherein the transformed plant retains all or all but one, two or three of the phenotypic and/or morphological and/or physiological characteristics of pepper variety NUN 89006 PPS or the progeny of said variety and contains the desired trait.

The disclosure also provides a plant or a cell of a plant comprising a desired trait produced by mutating a plant of variety NUN 89006 PPS or a cell thereof and selecting a plant the desired trait, wherein the mutated plant retains all or all but one of the phenotypic and morphological characteristics of said variety, optionally as described for each variety in in Tables 1, 2, and 3 and contains the desired trait and wherein a representative sample of seed of variety NUN 89006 PPS is deposited under Accession Number NCIMB 43267. In a further aspect, the desired trait is: yield, compact pepper, fruit quality, male sterility, herbicide tolerance, insect resistance, pest resistance, disease resistance, Powdery mildew resistance without necrosis, environmental stress tolerance, modified carbohydrate metabolism, modified protein metabolism, or ripening.

In one aspect, the disclosure provides a method for inducing mutation in pepper variety NUN 89006 PPS, comprising:
a) exposing the seed, plant or plant part or cell of pepper variety NUN 89006 PPS to a mutagenic compound or to radiation, wherein a representative sample of seed of said pepper variety is deposited under Accession Number NCIMB 43267;
b) selecting the seed, plant or plant part or cell of pepper variety NUN 89006 PPS, having a mutation; and
c) optionally growing and/or multiplying the seed, plant or plant part or cell of pepper variety NUN 89006 PPS, having the mutation.

The disclosure also provides a plant having one, two or three physiological and/or morphological characteristics which are different from those of pepper variety NUN 89006 PPS and which otherwise has all the physiological and morphological characteristics of said variety, wherein a representative sample of seed of said pepper variety is deposited under Accession Number NCIMB 43267. In particular, variants which differ from pepper variety NUN 89006 PPS, in none, one, two or three of the characteristics mentioned in Tables 1, 2, and 3 are encompassed.

A part of the plant of variety NUN 89006 PPS (or of progeny of said variety or of a plant having all physiological and/or morphological characteristics but one, two or three which are different from those of said variety) encompasses any cells, tissues, organs obtainable from the seedlings or plants, such as but not limited to: a pepper fruit or a part thereof, a cutting, hypocotyl, cotyledon, seed coat, pollen and the like. Such parts can be stored and/or processed further. The disclosure further provides for food or feed products comprising a part of the plant of variety NUN 89006 PPS, or a part of progeny of said variety, or a part of a plant having all but one, two or three physiological and/or morphological characteristics of pepper variety NUN 89006 PPS, comprising one or more of such parts, optionally processed (such as canned, chopped, cooked, roasted, in a sauce, in a sandwich, pasted, puréed or concentrated, juiced, frozen, dried, pickled, or powdered).

In one aspect, the disclosure provides for a haploid plant and/or a doubled haploid plant of variety NUN 89006 PPS, or of a plant having all but one, two or three physiological and/or morphological characteristics of pepper variety NUN 89006 PPS, or progeny of any of these. Haploid and doubled haploid (DH) plants can, for example, be produced by cell or tissue culture and chromosome doubling agents and regeneration into a whole plant. DH production chromosome doubling may be induced using known methods, such as colchicine treatment or the like). In one aspect, the method comprises inducing a cell or tissue culture with a chromosome doubling agent and regenerating the cells or tissues into a whole plant.

In another aspect, the disclosure comprises a method for making doubled haploid cells from haploid cells of pepper variety NUN 89006 PPS comprising doubling cells of with a doubling agent, such as a colchicine treatment (see, e.g., Nikolova V, Niemirowicz-Szczytt K (1996) Acta Soc Bot Pol 65:311-317).

In yet another aspect, the disclosure provides for haploid plants and/or doubled haploid plants derived from pepper variety NUN 89006 PPS that, when combined, make a set of parents of pepper variety NUN 89006 PPS. The haploid plant and/or the doubled haploid plant of variety NUN 89006 PPS can be used in a method for generating parental lines of pepper variety NUN 89006 PPS.

Using methods known in the art such as "reverse synthesis of breeding lines" or "reverse breeding", it is possible to produce parental lines for a hybrid plant such as pepper variety NUN 89006 PPS. Thus, a skilled person can take any individual heterozygous plant (called a "phenotypically superior plant" in Example 2 of US2015/0245570, hereby incorporated by reference in its entirety; pepper variety NUN 89006 PPS is such plant) and generate a combination of parental lines (reverse breeding parental lines) that, when crossed, produce pepper variety NUN 89006 PPS. It is not necessary that the reverse breeding parental lines are identical to the original parental lines. Such breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., pepper variety NUN 89006 PPS), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of pepper variety NUN 89006 PPS, which when crossed reconstitute the genome of pepper variety NUN 89006 PPS comprising:
a) defining a set genetic markers that are present a heterozygous form (H) in a partially heterozygous starting organism;
b) producing at least one further generation from the starting organism by self-pollination (e.g., F2 or F3 generation);
c) selecting at least one pair of progeny organisms in which at least one genetic marker from the set is present in a complementary homozygous forms (B vs. A, or A vs. B); and
d) optionally repeating steps b) and c) until at least one pair of progeny organisms that have complementary alleles for at least a subset of the genetic markers has been selected as parental lines for a hybrid The disclosure also provides a method for producing parental lines for pepper variety NUN 89006 PPS comprising: genetically characterizing a doubled haploid line from pepper variety NUN 89006 PPS to determine whether one or more genetic markers are present in a first homozygous form or in a second homozygous form in said line, wherein the one or more genetic markers are present in a heterozygous form in pepper variety NUN 89006 PPS; and selecting at least one pair of doubled haploid lines that have complementary alleles for the one or more the genetic markers, wherein each member of the pair is suitable as a parental line for a hybrid organism, optionally this method further comprises defining a set of genetic markers present in a heterozygous form in pepper variety NUN 89006 PPS; and producing doubled haploid lines from pepper variety NUN 89006 PPS. Doubled haploid lines generated as described herein can be used in such a method.

Thus, in one aspect, the disclosure relates to a method of producing a combination of parental lines of a plant of variety NUN 89006 PPS comprising making doubled haploid cells from haploid cells from said plant or a seed of that plant; and optionally crossing these parental lines to produce and collect seeds. In another aspect, the disclosure relates to a combination of parental lines produced by this method. In still another aspect, the combination of parental lines can be used to produce a seed or plant of variety NUN 89006 PPS, when these parental lines are crossed. In still another aspect, the disclosure relates to a combination of parental lines from which a seed or plant having all physiological and/or morphological characteristics of pepper variety NUN 89006 PPS (when the characteristics are determined at the 5% significance level for plants grown under the same conditions).

In another aspect, the disclosure provides a method of introducing a single locus conversion or single trait conversion or a desired trait into pepper variety NUN 89006 PPS comprising:
  a) obtaining a combination of a parental lines of pepper variety NUN 89006 PPS, optionally through reverse synthesis of breeding lines;
  b) introducing a single locus conversion, single trait conversion or a desired trait in at least one of the parents of step a; and
  c) crossing the converted parent with the other parent of step a to obtain seed of N pepper variety UN 89006 PPS.

A combination of a male and a female parental line of pepper variety NUN 89006 PPS can be generated by methods described herein, for example, through reverse synthesis of breeding lines.

In another aspect, the disclosure provides a method of introducing a single locus conversion or single trait conversion or a desired trait into pepper variety NUN 89006 PPS, comprising introducing a single locus conversion, single trait conversion, or a desired trait in at least one of the parents of pepper variety NUN 89006 PPS; and crossing the converted parent with the other parent of pepper variety NUN 89006 PPS to obtain seed of pepper variety NUN 89006 PPS.

The disclosure also provides a combination of parental lines which, when crossed, produce a seed or plant having all physiological and/or morphological characteristics of pepper variety NUN 89006 PPS but one, two or three which are different (when grown under the same environmental conditions), as well as a seed or plant having all physiological and/or morphological characteristics of pepper variety NUN 89006 PPS but one, two or three which are different (when the characteristics are determined at the 5% significance level for plants grown under the same conditions).

In another aspect, the step of introducing a single locus conversion, single trait conversion, or a desired trait in at least one of the parents comprises:
  a) obtaining a cell or tissue culture of cells of the parental line of pepper variety NUN 89006 PPS;
  b) genetically transforming or mutating said cells;
  c) growing the cells into a plant; and
  d) optionally selecting plants that contain the single locus conversion, the single trait conversion or the desired trait.

In another method, the step of introducing a single locus conversion, single trait conversion, or a desired trait in at least one of the parents comprises genetically transforming or mutating cells the parental line of pepper variety NUN 89006 PPS; growing the cells into a plant; and optionally selecting plants that contain the single locus conversion, the single trait conversion, or the desired trait.

In another aspect, the step of introducing a single locus conversion, single trait conversion, or a desired trait in at least one of the parents comprises:
  a) crossing the parental line of pepper variety NUN 89006 PPS, with a second pepper plant comprising the single locus conversion, the single trait conversion, or the desired trait;
  b) selecting F1 progeny plants that contain the single locus conversion, the single trait conversion, or the desired trait;
  c) crossing said selected progeny plants of step b) with the parental line of step a), to produce a backcross progeny plant;
  d) selecting backcross progeny plants comprising the single locus conversion, the single trait conversion or the desired trait and otherwise all or all but one, two or three of the morphological and physiological characteristics the parental line of step a) to produce selected backcross progeny plants; and
  e) optionally repeating steps c) and d) one or more times in succession to produce selected second, third or fourth or higher backcross progeny plants comprising the single locus conversion, the single trait conversion or the desired trait and otherwise all or all but one, two or three of the morphological and physiological characteristics the parental line of step a) to produce selected backcross progeny plants, when grown in the same environmental conditions.

The disclosure further relates to plants obtained by this method.

In the above methods, wherein the single locus conversion concerns a trait, the trait may be yield or pest resistance or disease resistance. In one aspect, the trait is disease resistance and the resistance is conferred to Cucumber Mosaic Virus, Curly Top Virus, Pepper Mild Mottle Virus, Potato Y Virus, Tobacco Etch Virus, Tobacco Mosaic Virus, Tomato Spotted Wilt Virus, Anthracnose (*Gloeosporium piperatum*), Bacterial Spot (*Xanthomonas vesicatoria*), Cercospora Leaf Spot (*Cercospora capsici*), Nematode (*Meloidogyne incognita acrita*), Phytophthora Root Rot (*Phytophthora capsici*), Ripe Rot (*Vermicularia capsici*), Southern Blight (*Sclerotium rolfsii*) and/or Verticillium Wilt (*Verticillium dahliae*). Other resistance genes, against pathogenic viruses, fungi, bacteria, nematodes, insects or other pests may also be introduced. In another aspect, the resistance is TSWV resistance.

Also provided is a plant part obtainable from variety NUN 89006 PPS, or from progeny of said variety or from a plant having all but one, two or three physiological and/or morphological characteristics which are different from those of said variety, or from a vegetatively propagated plant of variety NUN 89006 PPS (or from its progeny or from a plant having all or all but one, two or three physiological and/or morphological characteristics which are different from those of said variety): a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on pepper variety NUN 89006 PPS, or hypocotyl, cotyledon, a scion, a stock, a rootstock, a pistil, an anther, and a flower or a part thereof.

In another aspect, the disclosure provides a method of determining the genotype of a plant of the disclosure comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

The disclosure also provides for a food or feed product comprising or consisting of a plant part described herein. Particularly, the plant part is a pepper fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable pepper fruits are generally sorted by size and quality after harvest. Alternatively, the pepper fruits can be sorted by expected shelf life, pH or Brix.

Pepper variety NUN 89006 PPS may also be grown for use as rootstocks (stocks) or scions. Typically, different types of peppers are grafted to enhance disease resistance, which is usually conferred by the rootstock, while retaining the horticultural qualities usually conferred by the scion. It is not uncommon for grafting to occur between cultivated pepper varieties and related pepper species. Methods of grafting and vegetative propagation are well-known in the art.

In another aspect, the disclosure relates to a plant comprising a rootstock or scion of pepper variety NUN 89006 PPS.

All documents (e.g., patent publications) are herein incorporated by reference in their entirety, including the following cited references:

UPOV, "Guidelines for the Conduct of Tests for Distinctness, Uniformity and Stability, TG/76/8 (Geneva 2006, revised 2015 Mar. 25 and 2018 Sep. 20); world wide web at upov.int/under edocs/tgdocs/en/tg076.pdf.

US Department of Agriculture, Agricultural Marketing Service, "Objective Plant Description of Variety Pepper (*Capsicum* spp.)" world wide web at ams.usda.gov/services/plant-variety-protection/pvpo-c-forms, under pepper.

Acquaah, Principles of Plant Genetics and Breeding, 2007, Blackwell Publishing, ISBN-13: 978-1-4051-3646-4.

Ince, A. G., et al., "Genetic Relationship Within and Between *Capsicum* Species", Biochem Genet, 2010, vol. 48, pp. 83-95.

Kothari, S. L., et al., "Chili Peppers—A review on Tissue Culture and Transgenesis", Biotechnology Advances, 2010, vol. 28, pp. 35-48.

Martin, E., et al., "Identification of Markers Linked to Agronomic Traits in Globe Artichoke", Australian Journal of Crop Science, vol. 1, no. 2, pp. 43-46.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Rice, P., et al., "EMBOSS: The European Molecular Biology Open Software Suite", Trends in Genetics, 2000, vol. 16, Issue 6. pp. 276-277.

Sang-Gu, K., et al., "Callus Growth and Plant Regeneration in Diverse Cultivars of Cucumber", Plant Cell, Tissue and Organ Culture, 1988, vol. 12, pp. 67-74.

Tiwari, A., et al., "Parthenocarpic Potential in *Capsicum annum* L. is Enhanced by Carpelloid Structures and Controlled by Single Recessive Gene", BMC Plant Biology, 2011, vol. 11, pp. 2-14, DOI: 10.1186/1471-2229-11-143

Vos, P., et al., AFLP: A New Technique for DNA Fingerprinting 1995, Nucleic Acids Research, 1995, vol. 23, No. 21, pp. 4407-4414.

Wijnker, E., et al., Hybrid Recreation by Reverse breeding in *Arabidopsis thaliana*, Nature Protocols, 2014, vol. 9, pp. 761-772. DOI: doi: 10.1038/nprot.2014.049

U.S. Pat. No. 8,492,619

US2006/0037100

US2015/0245570

US2015/0126380

Development of Pepper Variety NUN 89006 PPS

The hybrid variety NUN 89006 PPS was developed from a male and female proprietary inbred line of Nunhems. The female and male parents were crossed to produce hybrid (F1) seeds of pepper variety NUN 89006 PPS. The seeds of pepper variety NUN 89006 PPS can be grown to produce hybrid plants and parts thereof (e.g., pepper fruit). The hybrid variety NUN 89006 PPS can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that pepper variety NUN 89006 PPS is uniform and stable.

Deposit Information

A total of 2500 seeds of the hybrid variety NUN 89006 PPS has been deposited according to the Budapest Treaty by Nunhems B.V. on Nov. 13, 2018, at the NCIMB Ltd., Ferguson Building, Craibstone Estate, Bucksburn, Aberdeen AB21 9YA, United Kingdom (NCIMB). The deposit is assigned NCIMB Number 43267. A deposit of pepper variety NUN 89006 PPS and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 U.S.C. § 2321 et seq.).

Characteristics of Pepper Variety NUN 89006 PPS

The most similar variety to NUN 89006 PPS is referred to as TP 2201, a variety from Femix Seeds. In Tables 1 and 2, a comparison between pepper variety NUN 89006 PPS and the Reference Variety are shown based on a trial in the USA during the trial season 2018. Trial location: Acampo, Calif., USA; Transplanting date: Nov. 29, 2018; Harvesting date: Mar. 5, 2019. In Table 3, the UPOV characteristics of pepper variety NUN 89006 PPS are shown. In Table 4, the distinguishing characteristics between pepper variety NUN 89006 PPS and the Reference Variety are shown.

A trial of 30 plants of each variety, from which at least 15 plants or plant parts were randomly selected and used to measure characteristics. For numerical characteristics, averages were calculated. For non-numerical characteristics, the type/degree were determined.

In one aspect, the disclosure provides a plant having the physiological and morphological characteristics of pepper variety NUN 89006 PPS, as presented in Tables 1, 2, and 3.

TABLE 1

Objective Description of Pepper Variety NUN 89006 PPS and the Reference Variety (USDA Descriptors)

| Characteristics | NUN 89006 PPS (Application Variety) | TP 2201 (Reference Variety) |
|---|---|---|
| Species: | | |
| 1 = C. annuum; 2 = C. frutescens; 3 = C. baccatum; 4 = C. chinense; 5 = Other (specify) | C. annuum | C. annuum |
| Maturity (in Region of Best Adaptability) | | |
| Days from transplanting until mature green stage | 55 days | NA |
| Days from transplanting until mature red or yellow stage | 65 days | NA |
| Plant (at maturity): | | |
| Plant Habit: | Semi-spreading | Semi-spreading |
| 1 = Compact; 2 = Semi-spreading; 3 = Spreading; 4 = Other | | |
| Plant Attitude: | Semi-erect | Erect to semi-erect |
| 1 = Erect; 2 = Semi-erect; 3 = Prostrate; 4 = Other | | |
| Plant Height (cm): | 58.8 | 62.1 |
| Length of Stem from Cotyledons to First Flower (cm): | 11.6 | 19.4 |
| Length of Third Internode (from soil surface) (mm): | 17.6 | 18.6 |

TABLE 1-continued

Objective Description of Pepper Variety NUN 89006 PPS and the Reference Variety (USDA Descriptors)

| Characteristics | NUN 89006 PPS (Application Variety) | TP 2201 (Reference Variety) |
|---|---|---|
| Basal Branches: | Few | Few |
| 1 = None; 2 = Few (2-3); 3 = Many (more than 3) | | |
| Branch Flexibility: | Rigid | Rigid |
| 1 = Willowy (Cayenne Long Red); 2 = Rigid (Yolo Wonder L) | | |
| Stem Strength (Breakage Resistance): | Intermediate | Intermediate |
| 1 = Weak; 2 = Intermediate; 3 = Strong | | |
| Leaves (at maturity): | | |
| Leaf Width (mm) | 141.9 | 133.7 |
| Leaf Length (mm) | 72.3 | 73.8 |
| Petiole Length (mm) | 82.4 | 77.7 |
| Mature Leaf Shape: | Lanceolate | Lanceolate |
| 1 = Lanceolate; 2 = Elliptic | | |
| Leaf Color: | Dark green (RHS N137C) | Dark green (RHS 139A) |
| 1 = Light Green; 2 = Medium Green; 3 = Dark Green; 4 = Purple; 5 = Other (specify) (RHS color chart value) | | |
| Leaf and Stem Pubescence: | Absent | Absent |
| 1 = Absent (Yolo Wonder L); 2 = Light; 3 = Moderate (Serrano); 4 = Heavy (Chili Piquin) | | |
| Margin Undulation: | Medium | Medium |
| 1 = Absent; 2 = Very Weak; 3 = Weak; 4 = Medium; 5 = Strong; 6 = Very Strong | | |
| Blistering: | Absent | Absent |
| 1 = Absent; 2 = Very Weak; 3 = Weak; 4 = Medium; 5 = Strong; 6 = Very Strong | | |
| Flowers: | | |
| Number of Flowers per Leaf Axil | 1 | 1 |
| Number of Calyx Lobes | 5.8 | 5.9 |
| Number of Petals | 5.7 | 5.7 |
| Flower Diameter (mm) | 25.7 | 22.5 |
| Corolla Color: | White | White |
| 1 = White; 2 = Purple; 3 = Other (Specify) | | |
| Corolla Throat Markings: | Purple | Purple |
| 1 = Yellow (Tan); 2 = Purple; 3 = Other (Specify) | | |
| Anther Color: | Yellow | Yellow |
| 1 = Yellow; 2 = Purple; 3 = Other (Specify) | | |
| Style Length: | Same as stamen | Same as stamen |
| 1 = Less Than Stamen; 2 = Same as Stamen; 3 = Exceeds Stamen | | |
| Fruit (at maturity): | | |
| Group: | Mini pointed | Mini pointed |
| 1 = Bell (Yolo Wonder L); 2 = Pimiento (Pimiento Perfection); 3 = Ancho | | |

TABLE 1-continued

Objective Description of Pepper Variety NUN 89006 PPS and the Reference Variety (USDA Descriptors)

| Characteristics | NUN 89006 PPS (Application Variety) | TP 2201 (Reference Variety) |
|---|---|---|
| (Mexican Chili); 4 = Anaheim Chili (Sandia); 5 = Cayenne (Cayenne Long Red); 6 = Cuban (Cubanelle); 7 = Jalapeno (Jalapeno); 8 = Small Hot (Serrano); 9 = Cherry (Sweet Cherry); 10 = Short Wax (Floral Gem); 11 = Long Wax (Sweet Banana); 12 = Tabasco (Tabasco); 13 = Habanero (Scotch Bonnet); 14 = Other | | |
| Immature Fruit Color: 1 = Light Green (Cubanelle); 2 = Medium Green (Long Thin Cayenne); 3 = Dark Green (Yolo Wonder L); 4 = Very Dark Green (Ancho Chili); 5 = Yellow (Yellow Belle); 6 = Purple (Violetta); 7 = Ivory (Twiggy); 8 = Other (RHS color chart value) | Medium green (RHS N137A) | Medium green (RHS 137A) |
| Mature Fruit Color: 1 = Red (Yolo Wonder L); 2 = Orange; 3 = Orange-Yellow (Golden Calwonder); 4 = Brown (Mulatto); 5 = Ivory; 6 = Green (Permagreen); 7 = Salmon; 8 = Lemon Yellow; 9 = Other (RHS color chart value) | Orange-yellow (RHS 23A) | Orange-yellow (RHS 17A) |
| Pungency: 1 = Sweet (Yolo Wonder L); 2 = Hot (Jalapeno) | Sweet | Sweet |
| Flavor: 1 = Mild Pepper Flavor; 2 = Moderate Pepper Flavor; 3 = Strong Pepper Flavor; 4 = Other | Mild pepper flavour | Mild pepper flavour |
| Fruit Glossiness: 1 = Dull; 2 = Moderate; 3 = Shiny | Moderate | Moderate |
| Surface Smoothness: 1 = Smooth (Yolo Wonder L); 2 = Rough (Long Thin Cayenne) | Smooth | Smooth |
| Fruit Position: 1 = Upright (Santaka); 2 = Horizontal; 3 = Pendent (Jalapeno) | Pendent | Pendent |
| Calyx Shape: 1 = Cup-shaped (Enveloping Fruit Base); 2 = Saucer-shaped (Flat, Non-Enveloping) | Saucer-shaped (flat, non-enveloping) | Saucer-shaped (flat, non-enveloping) |
| Calyx Diameter (mm) | 19.9 | 18.1 |
| Fruit Length (mm) | 89.7 | 67.1 |
| Fruit Diameter at Calyx Attachment (mm) | 32.1 | 33.9 |
| Fruit Diameter at Mid-point (mm) | 29.7 | 29.7 |
| Flesh Thickness at Mid-point (mm) | 4.7 | 4.8 |
| Average Number of Fruits per Plant | 13.2 | 16.7 |
| % Large fruits (Weight range: ___ to ___) | 73.3% (30-50) | 40% (30-50) |
| % Medium fruits (Weight range: ___ to ___) | 20% (20-29) | 26.7% (20-29) |
| % small fruits (Weight range: ___ to ___) | 6.7% (10-19) | 33.3% (10-19) |
| Average Fruit Weight (gm) | 35.2 grams | 24.8 grams |
| Fruit Base Shape: 1 = Cupped (Yolo Wond L); 2 = Rounded (Jalapeno) | Rounded | Rounded |
| Fruit Apex Shape: 1 = Pointed (Long Thin Cayenne); 2 = Blunt (Yolo Wonder L) | Pointed to blunt | Pointed |
| Fruit Shape: 1 = Bell (Yolo Wonder L); 2 = Conical (Pimiento); 3 = Elongate (Long Thin Cayenne); 4 = Oblong (Jalapeno) 5 = Oblate (Sunnybrook); 6 = Globe (Red Cherry); 7 = Other | Oblong | Oblong |
| Fruit Shape (Longitudinal Section, see attached pictures): 1 = Flattened; 2 = Round; 3 = Heart-shaped; 4 = Square; 5 = Rectangular; 6 = Trapezoid; 7 = Narrow Triangular 8 = Triangular; 9 = Horn-shaped | Moderately triangular | Moderately triangular |
| Fruit Shape (Cross Section, at Level of Placenta): 1 = Elliptic; 2 = Triangular; 3 = Quadrangular; 4 = Circular | Circular | Circular |
| Fruit Set: 1 = Scattered; 2 = Concentrated | Scattered | Scattered |
| Interloculary Grooves: 1 = Absent; 2 = Very Shallow; 3 = Shallow; 4 = Medium; 5 = Deep; 6 = Very Deep | Absent | Absent |
| % Fruits with one locule | 0 | 0 |
| % Fruits with two locules | 80 | 33.3 |
| % Fruits with three locules | 20 | 66.7 |
| % Fruits with four locules | 0 | 0 |
| % Fruits with five or more locules | 0 | 0 |
| Average Number of Locules | 2.20 | 2.67 |
| Pedicel Length (mm) | 27.1 | 25.7 |
| Pedicel Thickness (mm) | 6.3 | 6.1 |
| Pedicel Shape: 1 = Straight; 2 = Curved | Curved | Curved |
| Pedicel Cavity: 1 = Absent; 2 = Present | Absent | Absent |
| Seed | | |
| Seed Cavity Length (mm) | 63.9 | 51.7 |
| Seed Cavity Diameter (mm) | 18.4 | 19.6 |
| Placenta Length (mm) | 27.1 | 25.7 |
| Number of Seeds per Fruit | 46.9 | 7.20 |
| Gm per 1000 seeds | 8 grams | 7 grams |
| Seed Color: 1 = Yellow; 2 = Purple | Yellow | Yellow |
| Anthocyanin (at maturity) (1 = Absent; 2 = Weak; | | |

TABLE 1-continued

Objective Description of Pepper Variety NUN 89006 PPS and the Reference Variety (USDA Descriptors)

| Characteristics | NUN 89006 PPS (Application Variety) | TP 2201 (Reference Variety) |
|---|---|---|
| 3 = Moderate; 4 = Strong) | | |
| Seedling hypocotyl | Absent | Absent |
| Stem | Moderate | Moderate |
| Node | Moderate | Moderate |
| Leaf | Absent | Absent |
| Pedicel | Weak | Weak |
| Calyx | Absent | Absent |
| Fruit | Absent | Absent |

TABLE 2

Objective Description of Pepper Variety NUN 89006 PPS and the Reference Variety (Non-USDA descriptors)

| Characteristics | NUN 89006 PPS (Application Variety) | TP 2201 (Reference Variety) |
|---|---|---|
| Cotyledon length (mm) | 34.07 | 35.09 |
| Cotyledon width (mm) | 12.15 | 11.80 |
| Petiole width (mm) | 3.09 | 2.95 |

TABLE 3

UPOV Characteristics of Pepper Variety NUN 89006 PPS

| UPOV Characteristics | NUN 89006 PPS |
|---|---|
| Seedling: anthocyanin coloration of hypocotyl (10-14 days after sowing) (1 absent/9 present) | Present |
| Plant: habit (before maturity) (1 upright/2 semi-upright/3 prostrate) | Upright |
| Plant: shortened internode (in upper part) (1 absent/9 present) | Present |
| Plant: number of flowers per node (1 one or two/2 three or more) | One |
| Varieties with shortened internodes only: | None |
| Plant: number of internodes between the first flower and shortened internodes (1 none/2 one to three/3 more than three) | |
| Plant: anthocyanin coloration of nodes (before maturity) (1 absent/9 present) | Present |
| Plant: vigour (1 very weak/3 weak/5 medium/7 strong/9 very strong) | Strong |
| Stem: intensity of anthocyanin coloration of nodes (before maturity) (1 very weak/3 weak/5 medium/7 strong/9 very strong) | Medium |
| Stem: hairiness of nodes (1 absent or very weak/3 weak/5 medium/7 strong/9 very strong) | Absent or very weak |
| Leaf: color (1 dark green/2 green/3 yellow green) | Dark green |
| Leaf: intensity of green color (1 very light/3 light/5 medium/7 dark/9 very dark) | Dark |
| Leaf: shape (before maturity) (1 lanceolate/2 ovate/3 broad elliptic) | Lanceolate |
| Leaf: undulation of margin (before maturity) (1 absent or very weak/3 weak/5 medium/7 strong/9 very strong) | Medium |
| Leaf: pubescence (1 absent/9 present) | Absent |
| Leaf: blistering (before maturity) (1 very weak/3 weak/5 medium/7 strong/9 very strong) | Medium |
| Leaf: profile in cross section (before maturity) (1 strongly concave/2 moderately concave/3 flat/4 moderately convex/5 strongly convex) | Moderately concave |
| Leaf: glossiness (before maturity) (1 very weak/3 weak/5 medium/7 strong/9 very strong) | Weak |
| Peduncle: attitude (1 erect/2 semi-drooping/3 drooping) | Drooping |
| Flower: attitude of peduncle (1 erect/2 non-erect) | Non-erect |
| Flower: color before maturity (1 greenish white/2 yellow/3 green/4 purple) | Green |
| Flower: days to 50% flowering (from the date of sowing) (3 early/5 medium/7 late) | Medium |
| Flower: anthocyanin coloration in anther (1 absent/9 present) | Present |
| Fruit: color (before maturity) (1 greenish white/2 yellow/3 green/4 purple) | Green |
| Fruit: intensity of color (before maturity) (1 very light/3 light/5 medium/7 dark/9 very dark) | Medium |
| Bearing habit: Number of fruits per node (3 Solitary (only 1)/5 two to three/7 more than three) | One |
| Fruit: anthocyanin coloration (before maturity) (1 absent/9 present) | Present |
| Fruit: attitude (1 erect/2 horizontal/3 drooping) | Drooping |
| Fruit: shape in longitudinal section (at maturity) (1 oblate/2 circular/3 cordate/4 square/5 rectangular/6 trapezoidal/7 moderately triangular/8 narrowly triangular/9 hornshaped) | Moderately triangular |
| Fruit: curvature (1 absent/9 present) | Absent |
| Fruit: shape in cross section (at level of placenta) (1 elliptic/2 angular/3 circular) | Circular |
| Fruit: sinuation of pericarp at basal part (1 absent or very weak/3 weak/5 medium/7 strong/9 very strong) | Absent or very weak |
| Fruit: sinuation of pericarp excluding basal part (1 absent or very weak/3 weak/5 medium/7 strong/9 very strong) | Absent or very weak |
| Fruit: texture of surface (1 smooth or very slightly wrinkled/2 slightly wrinkled/3 strongly wrinkled) | Smooth |
| Fruit: color (at maturity) (1 yellow/2 orange/3 red/4 brown/5 green) | Yellow |
| Fruit: intensity of color (at maturity) (1 very light 3 light/5 medium/7 dark/9 very dark) | Medium |
| Fruit: color transition (3 one stage/5 two stages 7 more than two stages) | One stage |
| Fruit: glossiness (at maturity) (1 very weak/3 weak/5 medium/7 strong/9 very strong) | Medium |
| Fruit: shape of base (at maturity) (3 acute/5 round/7 sunken) | Round |
| Fruit: stalk cavity (1 absent/9 present) | Absent |
| Fruit: shape of apex (at maturity) (1 very acute/2 moderately acute/3 rounded/4 moderately depressed/5 very depressed) | Rounded |
| Fruit: depth of interlocular grooves (1 absent or very shallow/3 shallow/5 medium/7 deep) | Absent or very weak |
| Fruit: number of locules (1 predominantly two/2 equally two and three/3 predominantly three/4 equally three and four/5 predominantly four and more) | Equally two and three |
| Calyx: aspect (1 non enveloping/2 enveloping) | Non-enveloping |
| Fruit: capsaicin in placenta (1 absent/9 present) | Absent |
| Fruit: firmness (1 very weak/3 weak/5 medium/7 strong/9 very strong) | Medium |
| Time of beginning of flowering (first flower on second flowering node) (3 early/5 medium/7 late) | Medium |
| Time of maturity (1 very early/3 early/5 medium/7 late/9 very late) | Medium |

TABLE 4

Distinguishing Characteristics between Pepper Variety NUN 89006 PPS and the Reference Variety

| Characteristics | NUN 89006 PPS (Application Variety) | TP 2201 (Reference Variety) |
|---|---|---|
| Plant (at maturity): | | |
| Length of Stem from Cotyledons to First Flower (cm) | 11.6 | 19.4 |

TABLE 4-continued

Distinguishing Characteristics between Pepper Variety
NUN 89006 PPS and the Reference Variety

| Characteristics | NUN 89006 PPS (Application Variety) | TP 2201 (Reference Variety) |
|---|---|---|
| Length of Third Internode (from soil surface) (mm) | 17.6 | 18.6 |
| Plant Attitude | Semi-erect | Erect to semi-erect |
| Leaves (at maturity): | | |
| Leaf Width (mm) | 141.9 | 133.7 |
| Petiole width (mm) | 3.09 | 2.95 |
| Leaf Color | Dark green (RHS N137C) | Dark green (RHS 139A) |
| Flower: | | |
| Flower Diameter (mm) | 25.7 | 22.5 |
| Fruit: | | |
| Calyx Diameter (mm) | 19.9 | 18.1 |
| Fruit Length (mm) | 89.7 | 67.1 |
| Average Number of Fruits per Plant | 13.2 | 16.7 |
| Average Fruit Weight (gm) | 35.2 grams | 24.8 grams |
| Average Number of Locules | 2.20 | 2.67 |
| Immature Fruit Color | Medium green (RHS N137A) | Medium green (RHS 137A) |
| Mature Fruit Color | Orange-yellow (RHS 23A) | Orange-yellow (RHS 17A) |
| Seed: | | |
| Seed Cavity Length (mm) | 63.9 | 51.7 |
| Placenta Length (mm) | 27.1 | 25.7 |
| Number of Seeds per Fruit | 46.9 | 7.20 |

The invention claimed is:

1. A plant, plant part, or seed of pepper variety NUN 89006 PPS, wherein a representative sample of seed of said pepper variety is deposited under Accession Number NCIMB 43267.

2. The plant part of claim 1, wherein said plant part is a fruit, a leaf, pollen, an ovule, a cell, a scion, a root, a rootstock, a cutting, or a flower.

3. A seed that produces the plant of claim 1.

4. A pepper plant having all of the physiological and morphological characteristics of the plant of claim 1.

5. A pepper plant which does not differ from the plant of claim 1, when the numerical characteristics are determined at the 5% significance level when grown under the same environmental conditions, and wherein a representative sample of seed of said pepper variety is deposited under Accession Number NCIMB 43267.

6. A tissue or cell culture comprising regenerable cells of the plant of claim 1.

7. The tissue or cell culture according to claim 6, comprising cells or protoplasts derived from a plant part suitable for vegetative reproduction, wherein the plant part is a meristem, a cotyledon, a hypocotyl, pollen, a leaf, an anther, a root, a root tip, a pistil, a petiole, a flower, a fruit, a stem, or a stalk.

8. A pepper plant regenerated from the tissue or cell culture of claim 7, wherein the regenerated plant has all of the physiological and morphological characteristics of pepper variety NUN 89006 PPS, when the numerical characteristics are determined at the 5% significance level for plants grown under the same environmental conditions, and wherein a representative sample of seed of pepper variety is deposited under Accession Number NCIMB 43267.

9. A method of producing the plant of claim 1, said method comprising vegetatively propagating at least a part of the plant of variety NUN 89006 PPS, wherein a representative sample of seed of said pepper variety is deposited under Accession Number NCIMB 43267.

10. The method of claim 9, wherein said vegetative propagation comprises regenerating a whole plant from said part of the plant of variety NUN 89006 PPS, wherein a representative sample of seed of said pepper variety is deposited under Accession Number NCIMB 43267.

11. The method of claim 9, wherein said part is a cutting, a cell culture, or a tissue culture.

12. A vegetatively propagated plant produced by the method of claim 9, wherein the plant has all of the physiological and morphological characteristics of the plant of variety NUN 89006 PPS, when the numerical characteristics are determined at the 5% significance level for plants grown under the same conditions, and wherein a representative sample of seed of said pepper variety is deposited under Accession Number NCIMB 43267.

13. A method of producing a pepper plant, said method comprising crossing the plant of claim 1 with itself or with a second pepper plant at least once, selecting a progeny pepper plant from said crossing and optionally allowing the progeny pepper plant to form seed, wherein said selected progeny pepper plant has all of the physiological and morphological characteristics of the plant of variety NUN 89006 PPS when grown under the same environmental conditions, and wherein a representative sample of seed of said pepper variety is deposited under Accession Number NCIMB 43267.

14. A method of introducing a desired trait into the plant of claim 1, comprising transforming the plant of claim 1 with a transgene that confers the desired trait, wherein the plant comprises the desired trait and otherwise has all of the physiological and morphological characteristics of the plant of claim 1.

15. The plant of claim 1, further comprising a single locus conversion, wherein said plant otherwise has all of the morphological and physiological characteristics of the plant of variety NUN 89006 PPS, when the numerical characteristics are determined at the 5% significance level for plants grown under the same environmental conditions, wherein a representative sample of seed of said pepper variety is deposited under Accession Number NCIMB 43267, and wherein the single locus conversion confers male sterility, herbicide tolerance, pest resistance, environmental stress resistance, modified carbohydrate metabolism, modified protein metabolism or ripening.

16. A method of making doubled haploid cells of pepper variety NUN 89006 PPS, said method comprising making double haploid cells from the plant or seed of pepper variety NUN 89006 PPS, wherein a representative sample of seed of said pepper variety is deposited under Accession Number NCIMB 43267.

17. A plant comprising the scion or rootstock of claim 2.

18. A container comprising the plant, plant part, or seed of claim 1.

19. A food, or a feed product, or a processed product comprising the plant part of claim 2, wherein the plant part comprises at least one cell of pepper variety NUN 89006 PPS.

20. A method of producing a pepper plant having a desired trait, wherein the method comprises mutating a plant or plant part of variety NUN 89006 PPS and selecting a plant with a desired trait, wherein the mutated plant otherwise retains all or all but one, two, or three of the physiological and morphological characteristics of pepper variety NUN 89006 PPS, when the numerical characteristics are determined at the 5% significance level for plants grown under the same environmental conditions, wherein a representative sample of seed of said pepper variety NUN 89006 PPS is deposited under Accession Number NCIMB 43267, and wherein the desired trait is male sterility, herbicide tolerance, pest resistance, environmental stress resistance, modified carbohydrate metabolism, modified protein metabolism or ripening.

21. A method of producing a pepper fruit, said method comprising growing the plant of claim 1 until it sets at least one fruit and collecting the fruit.

22. The fruit produced by the method of claim of claim 21.

23. A container comprising the fruit or part thereof produced by the method of claim 21.

* * * * *